Aug. 12, 1958 W. E. LAMMERTS Plant Pat. 1,742
ROSE PLANT
Filed Dec. 23, 1957
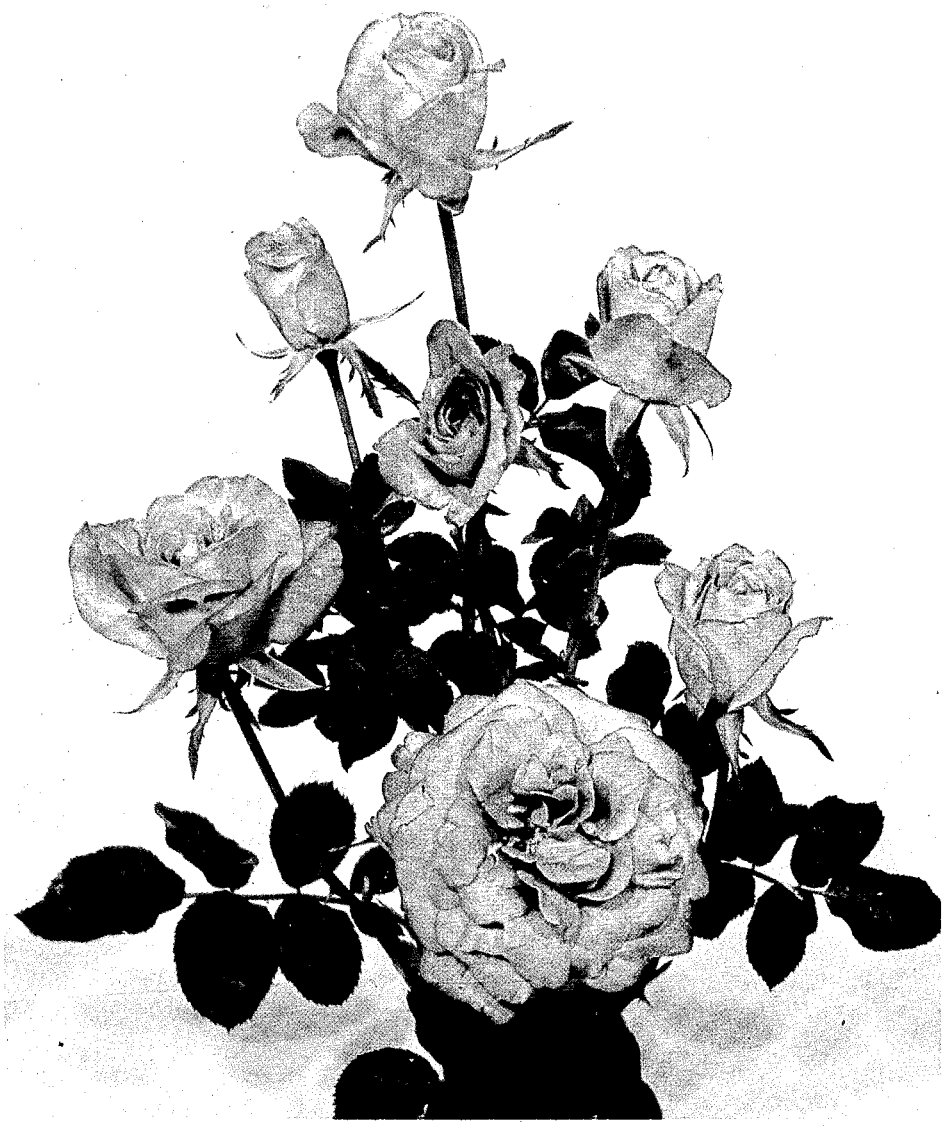
Inventor.
W. E. Lammerts
By: Robert Cobb
Attorneys.

United States Patent Office

Plant Pat. 1,742
Patented Aug. 12, 1958

1,742

ROSE PLANT

Walter E. Lammerts, Livermore, Calif., assignor, by mesne assignments, to Germain's, Inc., Van Nuys, Calif., a corporation of California Application December 23, 1957, Serial No. 704,851

1 Claim. (Cl. 47—61)

The present invention relates to a new and distinct variety of rose plant of the hybrid tea class, which was originated by me by crossing the variety "Charlotte Armstrong" (Plant Patent No. 455) with an unnamed and unpatented first generation hybrid of "Charlotte Armstrong" × "Floradora" (unpatented).

As the result of this breeding, I have produced a new rose variety which is distinctly different from both parents, as well as from all other varieties of its class of which I am aware, as evidenced by the following characteristics which are outstanding in the new variety and represent a new and unusual combination:

(1) Bushy habit of growth;

(2) Glossy green foliage, with the new growth heavily pigmented with anthocyanin and giving the new growth and foliage a bronze appearance;

(3) Free-branching and cluster-flowering habit, with both the individual flower stems and the cluster flower stems of good length and suitable for cut flower use;

(4) Dark red, urn-shaped flower buds;

(5) Glowing dark red open flowers, ranging in general color tonality from Currant Red to dark Rose Red and having an almost fluorescent quality;

(6) Good color retention of the flowers, and an unusually small magenta color content; and (7) Upright habit of the flower petals which surround and cover the stamens and pistils.

In comparison with the parent variety "Charlotte Armstrong," the foliage of my new variety has a much more glossy green color, while the new growth is much more heavily pigmented with anthocyanin, giving a more bronze appearance to the new growth and foliage. Still further, the flower buds are darker red in color and open into flowers which are much darker in color than those of this parent whose buds are usually cherry colored and whose open flowers are in the lighter range of Rose Red color. While the buds of this parent are much longer, they are not as urn-shaped as those of the new variety, and the flowers of the new variety hold their color longer without turning blue than the flowers of "Charlotte Armstrong." In fact, the flowers of my new variety have much less magenta color than those of any red rose variety of which I am aware.

The plants of my new variety tend to branch and form flower clusters more freely than "Charlotte Armstrong," and the flowers are borne both singly and in clusters on stems varying in length from 6 to 12 inches, and hence are suitable for cut flower use. In this respect, the new variety shows the influence of its floribunda grandparent, "Floradora" and accordingly, it fits into the new grandiflora class, but is much bushier than the sister seedling of the pollen parent "Queen Elizabeth" (Plant Patent No. 1,259), but is not as tall and compact in its habit of growth.

One of the most outstanding characteristics of my new variety is the unusual glowing quality of the Currant Red flower color which tends to be almost fluorescent in appearance.

Asexual reproduction of my new variety by budding, as performed by me at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color.

The following is a detailed description of my new variety, with color terminology in accordance with the Horticultural Colour Chart of the British Colour Council, except where general color terms of ordinary dictionary significance are obvious, as based upon observations of speciments grown at Livermore, California:

Type: Hardy; tall; bush; outdoor; seedling; for garden decoration.

Class: Hybrid tea.

Breeding: Seedling.

*Seed parent.*—"Charlotte Armstrong."

*Pollen parent.*—An unnamed first generation hybrid of "Charlotte Armstrong" × "Floradora."

Propagation: Holds its distinguishing characteristics through succeeding propagations by budding.

*Flower*

Flowers Borne: Both singly and several to stem; in rounded clusters; on normally strong stems of medium length.

Quantity of Bloom: Abundant, outdoors.

Continuity: Continuous.

Fragrance: Moderate. Nature—spicy.

Bud:

*Peduncle.*—Medium length; medium caliper; erect; stiff; almost smooth; with few gland-tipped hairs and prickles of reddish green color. Color—Lettuce Green, Plate 861/1.

*Before calyx breaks.*—Size—medium. Form—short; pointed; without foliaceous appendages on the surface of the bud; with slender, entire foliaceous parts extending beyond the tip of the bud equal to ¼ of its length. Color—Chrysanthemum Crimson, Plate 824/1.

*As calyx breaks.*—Color—Chrysanthemum Crimson, Plate 824/1.

*As first petal opens.*—Size—medium large. Form—medium long; urn-shaped. Color: outside—Currant Red, Plate 821/2; inside—Currant Red, Plate 821/1.

*Opening.*—Opens up well, but is retarded in opening by cold and wet weather.

Bloom:

*Size (when fully open).*—Medium large; from 4 to 5 inches.

*Petalage.*—Double; from 25 to 34 petals, with from 9 to 11 petaloids; arranged regularly.

*Form.*—High-centered at first, but becoming cupped; petals being at first loosely rolled inward, but later becoming loosely rolled outward at maturity.

Petals:

*Texture.*—Soft. Inside—velvety. Outside—satiny.

*Shape.*—Outside—obovate; apex having one or two notches. Intermediate—obovate; apex having one or two notches. Inside—obovate; irregular; apex having from one to three notches.

This description of a newly opened flower was made from a rose grown outdoors in the month of June, at Livermore, California:

*Color.*—Outer petal: outside surface—from Rose Red, Plate 724 to Tyrian Purple, Plate 727/2; inside surface—from Rose Red, Plate 724 to Tyrian Purple, Plate 727. Intermediate petal: outside surface—from Rose Red, Plate 724 to Tyrian Purple, Plate 727/2; inside surface—from Currant Red, Plate 821/2 to Rose Red, Plate 724. Inner petal: outside surface—Rose Red, Plate 724; inside surface—from Currant Red, Plate 821/2 to Rose Red, Plate 724.

This description was made from a rose grown outdoors that was open for 3 days in the month of June, at Livermore, California:

*Color.*—Outer petal: outside surface—from Rose Red, Plate 724 to Tyrian Purple, Plate 727; inside surface—from Rose Red, Plate 724 to Tyrian Purple, Plate 727. Inner petal: outside surface—from Rose Red, Plate 724 to Tyrian Purple, Plate 727; inside surface—from Rose Red, Plate 724 to Tyrian Purple, Plate 727.

*General color effect.*—Newly opened flower—from Currant Red, Plate 821/2 to Rose Red, Plate 724. 3-days open—from Rose Red, Plate 724 to Tyrian Purple, Plate 727.

*Behaviour.*—Drop off cleanly; very little fading; in cold or wet weather, color changes more to Rose Red, Plate 724 and Tyrian Purple, Plate 727.

*Flower longevity.*—On bush in garden—5 days in June. Cut roses grown outdoors and kept at living-room temperatures—5 days in June.

*Reproductive organs*

Stamens: Many; arranged irregularly about pistils; mixed with petaloids.

Filaments: Short; many; most with anthers. Color—Lemon Yellow, Plate 4, tinged with Carrot Red, Plate 612.

Anthers: Small; open at various times. Color—Orange Buff, Plate 507.

Pollen: Sparse. Color—Cadmium Orange, Plate 8.

Pistils: Many.

Styles: Uneven; short; thin; loosely columnar.

Stigma: Color—Naples Yellow, Plate 403/1.

Ovaries: All enclosed in calyx.

Hips: Usually shrivel or drop before maturity.

Sepals: Permanent, but last only as long as the hips; spear-shaped; recurved. Color—Lavender Green, Plate 000761.

Seeds: None.

*Plant*

Foliage:

*Leaves.*—Compound of 5–7 leaflets; very abundant; large; glossy.

*Leaflets.*—Shape — oval. Apex — acute. Base—round. Margin—simply and irregularly serrate.

*Color.*—Mature: upper surface—Parsley Green, Plate 00962; under surface—Lavender Green, Plate 000761. Young: upper surface—Parsley Green, Plate 00962, heavily tinged with bronze; under surface—Lavender Green, Plate 000761, with almost a completely bronze overtone.

*Rachis (the supporting stem of the compound leaf).*—Medium heavy. Upper side—smooth; grooved. Under side—sparsely prickly.

*Stipules.*—Medium length; narrow; wide (sometimes up to ½ inch broad at base with margin very serrate); with long points turning out at an angle of more than 45°; recurved toward the stem.

*Disease resistance.*—Good resistance to mildew, but somewhat subject to rust, as compared with other varieties grown under comparable cultural conditions at Livermore, California.

Growth:

*Habit.*—Bushy; upright; many branches.

*Growth.*—Free; vigorous.

*Canes.*—Heavy.

*Main stems.*—Color—Spinach Green, Plate 0960/3, often lightly tinged with bronze. Thorns—many; long; straight; with long, narrow base. Prickles—many; color—bronze red. Hairs—few; usually gland-tipped; color—bronze red.

*Branches.*—Color—Spinach Green, Plate 0960/3, usually heavily tinged with bronze. Thorns—many; long; straight; with long, narrow base. Prickles—many; color — reddish. Hairs — few; usually gland-tipped; color—reddish.

*New shoots.*—Color—near Spinach Green, Plate 0960/3, very heavily tinged with bronze on upper side. Thorns—Many; long; straight; with long, narrow base. Prickles—many; color—reddish. Hairs—few; color—reddish.

I claim:

A new and distinct variety of rose plant of the hybrid tea class, substantially as herein shown and described, characterized particularly as to novelty by its bushy habit of growth, glossy green foliage, with the new growth heavily pigmented with anthocyanin and giving the new growth and foliage a bronze appearance, its free-branching and cluster-flowering habit, with both the individual flower stems and the cluster flower stems of good length and suitable for cut flower use, its dark red urn-shaped flower buds, its glowing dark red open flowers, ranging in general color tonality from Currant Red to dark Rose Red, and having an almost fluorescent quality, the good color retention of its flowers and their unusually small magenta color content, and the upright habit of its flower petals which surround and cover the stamens and pistils.

No references cited.